United States Patent
Ament et al.

(10) Patent No.: US 7,220,386 B2
(45) Date of Patent: May 22, 2007

(54) ON-BOARD FUEL PROPERTIES MEASUREMENT FOR ENGINE MANAGEMENT

(75) Inventors: Frank Ament, Troy, MI (US); Sam R. Reddy, West Bloomfield, MI (US)

(73) Assignee: General Motors Corporation, Detroit, MI (US)

( * ) Notice: Subject to any disclaimer, the term of this patent is extended or adjusted under 35 U.S.C. 154(b) by 657 days.

(21) Appl. No.: 10/388,121

(22) Filed: Mar. 13, 2003

(65) Prior Publication Data

US 2004/0180447 A1 Sep. 16, 2004

(51) Int. Cl.
*G01N 27/00* (2006.01)

(52) U.S. Cl. ............ 422/82.02; 422/73; 422/35.02

(58) Field of Classification Search .......... None
See application file for complete search history.

(56) References Cited

U.S. PATENT DOCUMENTS 6,360,726 B1 *  3/2002  Javaherian ............ 123/491
6,588,253 B2 *  7/2003  Lambert et al. ........ 73/53.01
2003/0089164 A1 *  5/2003  Bonadies et al. ........ 73/113
2003/0213293 A1 * 11/2003  Lee et al. ............ 73/118.1

* cited by examiner

Primary Examiner—Yelena G. Gakh
(74) Attorney, Agent, or Firm—Christopher DeVries (57) ABSTRACT

A narrow test chamber has at least one heater immersed with its major faces parallel to the fuel surface, part way up the chamber. Heater resistance increases non-linearly as a critical temperature is reached. When the heater is energized, fuel begins to evaporate. Heater temperature remains below the critical temperature until the fuel level drops to or just below the heater level, whereupon heater temperature rises quickly to the critical temperature and heater current drops sharply. The time t1 required to reach this point and the heater current or energy consumed vary according to the fuel distillation Drivability Index (DI). The DI is determined from the measured heater current and t1 or from differential measurement of t1 for two heaters mounted one above the other, by calculation or from a look-up table. The DI value is then used to control engine operation to reduce pollution and improve performance.

7 Claims, 6 Drawing Sheets

ON-BOARD FUEL PROPERTIES MEASUREMENT FOR ENGINE MANAGEMENT

FIELD OF THE INVENTION

This invention relates to on-board measurement of liquid fuel properties, more particularly to the fuel distillation Drivability Index (DI), and use of such properties to improve engine management and reduce undesirable exhaust emissions.

BACKGROUND OF THE INVENTION

Spark ignition engines operate by igniting a mixture of air and fuel vapors. Gasoline is the most common fuel used today, but this invention is not limited merely to gasoline. The tendency of the fuel to vaporize is important for efficient engine operation and low emission of pollutants. Fuels that do not vaporize readily can cause hard starting, poor drivability during cold operation, excessive byproduct emission and other problems. Conversely, fuel that vaporizes too readily in fuel pumps, fuel lines, carburetors or fuel injectors, etc., can cause decreased liquid flow to the engine and also result in poor engine operation and excess pollutants.

There are several measures of fuel volatility in common use, as for example, the Reid Vapor Pressure (RVP), the distillation Drivability Index (DI), and the Vapor-Liquid Ratio (VLR) or Air Fuel Ratio (A/F). Standard techniques for measuring various fuel properties are provided by the American Society for Testing Materials (ASTM), 100 Barr Harbour Drive, P.O. Box C700, West Conshohocken, Pa. 19428-2959 USA, and are well known in the art. The ASTM also publishes standards for fuels to meet in the USA.

For example, vehicle fuel specification ASTM D-4814 defines vapor pressure and distillation class requirements for six gasoline volatility classes: AA, A, B, C, D, and E. The specification assigns a vapor pressure/distillation profile class each month to each geographical area (state or portion of a state) in the USA based on altitude and the expected ambient temperature range. This data may be conveniently summarized using the distillation Drivability Index defined by the following equation:

$$DI = 1.5*(T_{10}) + 3.0*(T_{50}) + (T_{90}) \qquad [1]$$

where $(T_{10})$, $(T_{50})$ and $(T_{90})$ are the temperatures in degrees Fahrenheit for 10%, 50% and 90%, respectively, of the evaporated fuel in a distillation test cell. These six volatility classes correspond to gasoline DI values ranging from about 1000 to over 1300. According to a report published by the Chevron Corporation, in 1989 the winter and summer average DI values for gasoline in the USA were about 1030 and about 1127 respectively. It is apparent that fuel properties, as reflected for example in the different DI values, vary substantially during the year, in different geographic locations and with other factors. In order for an engine to run efficiently, smoothly and with improved emissions, it is desirable for the engine control system to adapt to this wide range of fuel properties.

Engine control systems of the prior art have dealt with this variation in fuel properties by using feed-back. For example, measuring the properties of the engine exhaust stream and using this information to adjust the amount of air and injected fuel, engine timing and other parameters so that the A/F ratio more closely approaches stoichiometry. While this works well enough in steady state, it does not work well, for example, during cold starts before the engine and exhaust system have reached normal operating temperatures. During these periods, the engine control system usually relies on stored values for the fuel properties, as for example, one or more stored DI numbers. The stored values must be chosen to reflect the worst-case fuel properties that the engine will likely encounter during any season, altitude, geographical region, ambient temperature, and so forth. Thus, the DI number used by the engine control system, for example, from cold-start through the end of the warm-up period, does not necessarily correspond to the actual properties of the fuel being burned. This can result in poor engine performance and/or excessive hydrocarbon emissions, which are undesirable.

Thus, a need continues to exist for a system for providing the engine control system with information on the volatility properties of the fuel actually on-board the vehicle and about to be burned by the engine. Additional features will become apparent to one skilled in the art based on the foregoing background of the invention, the following detailed description of a preferred embodiment and the appended claims.

SUMMARY OF THE INVENTION

According to an exemplary embodiment of the invention, there is provided an on-board fuel properties test cell comprising a chamber for receiving a representative sample of on-board fuel; one or more heaters located in the chamber and having a non-linear temperature coefficient of resistance that takes on a large positive value as the heater temperature approaches a critical temperature, the one or more heaters being located in the chamber so as to evaporate a predetermined portion or portions of the fuel sample when the critical temperatures of the one or more heaters are reached.

According to another exemplary embodiment of the invention, there is provided an on-board engine fuel properties measurement system further comprising, a test cell as noted above and a circuit for measuring electrical properties of the one or more heaters and determining the elapsed time until a rapid heater resistance increase occurs, a computer for receiving the measured electrical properties and elapsed time and for determining a fuel volatility index for the on-board fuel using one or more parameters determined at least in part by the electrical properties and elapsed time, and an apparatus for transmitting the calculated fuel volatility index to an engine management system.

According to yet another embodiment of the invention, there is provide a method for improving engine performance comprising the steps of, placing fuel in the test cell, determining the initial temperature of the fuel being tested, energizing at least one heater within the test cell, measuring electrical current flowing to the heater, using the measured values of the heater current until the heater reaches its critical temperature together with known fuel parameters to determine a distillation Drivability Index of the fuel in the test cell, and transmitting such Drivability Index value to an engine control system.

BRIEF DESCRIPTION OF THE DRAWINGS

The following drawings are illustrative of exemplary embodiments and therefore do not limit the scope of the invention. They are presented to assist in providing a proper understanding of the invention. The drawings are not to scale, unless so stated, and are intended for use in conjunction with the explanations in the following detailed description. The present invention will hereinafter be described in conjunction with the accompanying drawings, wherein like referenced numerals denote like elements, and.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the drawings.

Figure 1:
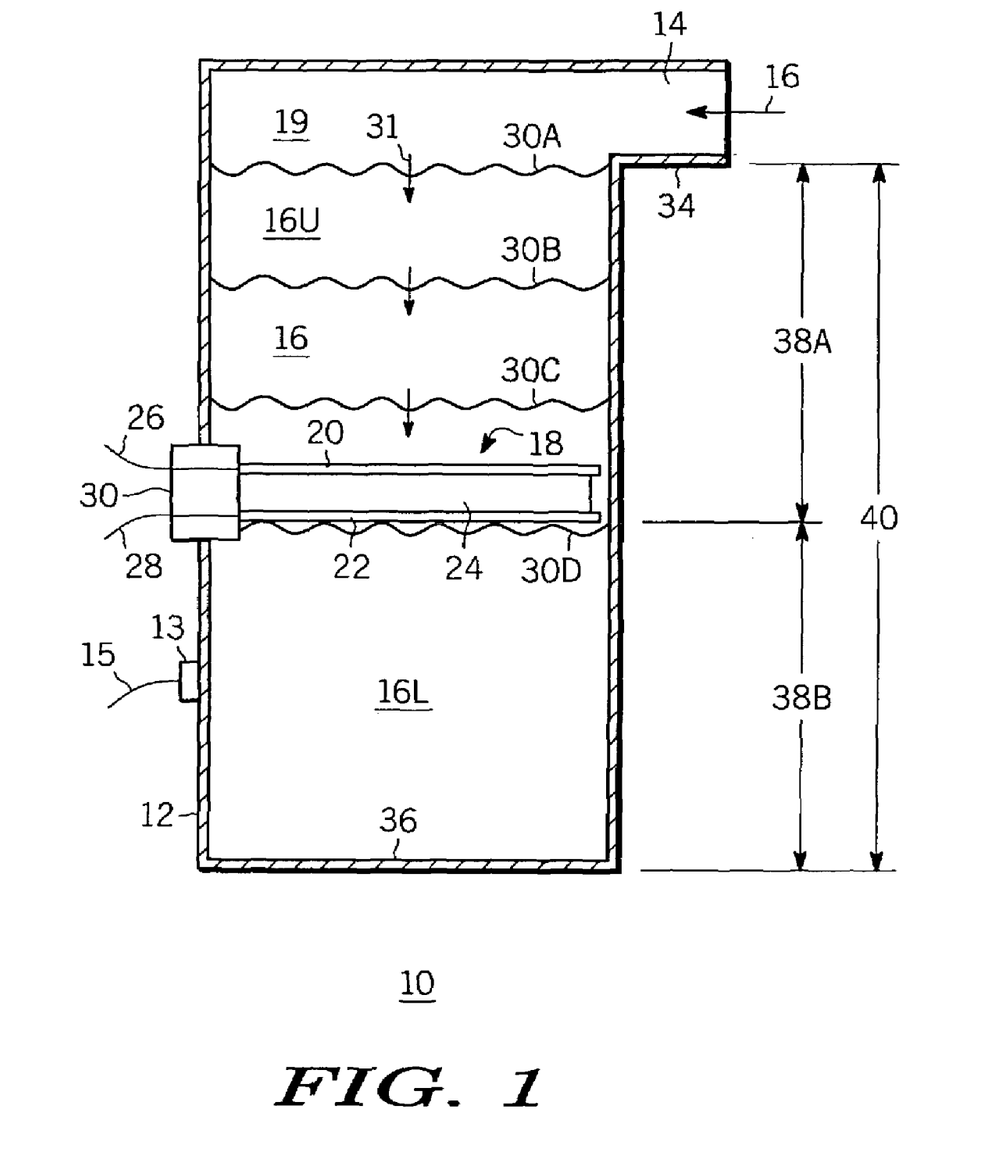
FIG. 1 is a simplified cross-sectional schematic diagram of a fuel test cell according to an exemplary embodiment of the present invention.

FIG. 1 is a simplified cross-sectional schematic diagram illustrating fuel properties test cell 10 according to an exemplary embodiment of the present invention. Test cell 10 has housing 12 with opening 14 through which fuel 16 is introduced. Opening 14 of test cell 10 serves at least two functions. It allows fuel 16 to be introduced into test cell 10 and also provides for an escape of fuel vapor 19 generated within test cell 10. Temperature sensor 13 with electrical lead 15 is provided to measure the temperature of fuel 16 in test cell 10. However, as will be explained later, temperature sensor 13 is not essential since the temperature of fuel 16 can be determined by other methods and apparatus.

Located within test cell 10 is heater 18. Heater 18 has upper electrode 20 and lower electrode 22, typically made of metal, but other conductive materials can also serve. Preferably, conductive metals are used that are reasonably unaffected by fuel 16. Steel and aluminum are examples of suitable materials for electrodes 20, 22. Resistive element 24 is sandwiched between electrodes 20, 22. As will be subsequently explained in more detail, it is desirable that resistive element 24 and therefore heater 18 have a non-linear temperature coefficient of resistance. In particular, it is desirable that resistive element 24 and heater 18 have a temperature coefficient of resistance that is positive and increases rapidly with increasing heater temperature as a critical temperature $T_C$ is approached. Ceramic materials with a region of operation having comparatively large non-linear Positive Temperature Coefficient (PTC) of resistance values are particularly suitable for resistive element 24. Electrical leads 26, 28 connect to electrodes 20, 22, respectively, via insulating feed-through 30. Feed through 30 preferably provides a liquid-tight seal to housing 12. Heater 18 is preferably oriented so that the principal faces, e.g., electrodes 20, 22, are at least approximately parallel with surface 30A–30D of fuel 16.

Test cell 10 is filled with fuel 16 to initial level 30A. Heater 18 heats fuel 16 so that the portion 16U of fuel 16 above heater 18 is vaporized creating fuel vapor 19 above liquid fuel 16. As fuel portion 16U is converted to vapor 19 and escapes from opening 14, level 30A of fuel 16 begins to drop. It is desirable that heater 18 be placed with its lower electrode about mid-way between inlet level 34 and bottom level 36 of housing 12, that is, so that distances 38A, 38B are about equal to half of distance 40. With this arrangement, heater 18 can evaporate approximately fifty percent of fuel 16 in test cell 10 during a measurement cycle. However, heater 18 can be located at other heights within cell 10, for example, so as to evaporate about 20–80% of fuel 16, more preferably 30–70% of fuel 16, even more preferably about 40–60% of fuel 16, and most preferably about 50% of fuel 16 during a measurement cycle. Thus, heater 18 can be placed at levels having corresponding percentages of the distance between upper level 34 and lower level 36 of test cell 10. Further, as will be explained in further detail later, more than one heater can be used, and placed at different levels within the test cell (see for example, FIGS. 5–6).

When test cell 10 is filled with fuel 16, for example to level 30A, and heater 18 begins operating, heater 18 is at least partially immersed, more preferably substantially immersed, and most preferably completely immersed in fuel 16 and the temperature reached by heater 18 is determined by the rate of heat loss to liquid fuel 16 and the heat of vaporization of fuel 16. Since solid-liquid thermal coupling is relatively efficient, the temperature of heater 18 stays relatively close above the fractional distillation temperature of fuel 16 once distillation commences. As the lower temperature fuel fractions distill off, liquid level 30A drops progressively to levels 30B, 30C and so forth and the temperatures of fuel 16 and heater 18 slowly rise. This continues until the level of fuel 16 drops to level 30D at or just below heater 18. When at least a portion of the heater 18 is no longer immersed in fuel 16, and generally when a substantial portion or about all of the heater 18 is no longer immersed in fuel, its temperature begins to rise much more rapidly since the solid-liquid thermal contact between heater 18 and fuel 16 is replaced by the much higher thermal impedance contact between heater 18 and fuel vapor 19. At that point, distillation of fuel 16 slows markedly even though the temperature of heater 16 is rising rapidly.

What is most desirable for heater 18 is that resistive element 24 has a non-linear PTC of resistance that increases very rapidly as the heater temperature approaches the critical value ($T_C$). Then the measurement process can be effectively self-limiting. In a first exemplary embodiment of the present invention with heater 18 located about at the mid-point of cell 10, the critical temperature arrives quickly once about 50% of fuel 16 has vaporized and liquid-solid contact to heater 18 is lost. At this point, heater 18 effectively shuts off. The $T_C$ associated with the non-linear behavior of heater 18 is desirably chosen to be above $T_{50}$ for the range of fuels to be encountered, but other higher or lower values can also be used, e.g., $T_C$ values related to $T_{10}$ to $T_{90}$ or higher or lower depending on how much fuel is being vaporized in the test measurement and the location of heater 18 within test cell 10 and whether or not multiple heaters are used and the anticipated fuel mix composition. With this arrangement, it is not necessary to use temperature controls, temperature limiters, fuses, and so forth, thereby greatly reducing the cost of test cell 10.

Suitable non-linear PTC heaters, generally referred to as PTC Thermistor heaters with $T_C$ values in a useful range for spark ignition engine fuels are available from the Sunlead Electrical Corporation, 5F, No. 41, Lane 221, Kang Chien Road, Taipei City, Taiwan, ROC or Lunqi Electronic Co., Ltd, Victon Technology Electronic Ltd., Industrial Area of Xia-Bian District, Hou-Jie Dong-Guan, Guang-Dong, P. R. China.

For example, a PTC Thermistor heater using a $BaTiO_3$ ceramic resistance element exhibits a resistance of the order of about $10^2$ ohms at about 25° C. and a flat or slightly Negative Temperature Coefficient (NTC) of resistance over the temperature range from about 25 to above about 100° C., and then shows a very large, non-linear increase in resistance to over $10^5$ ohms in the range of about 125–175° C., peaking at almost $10^6$ ohms at about 200° C. The very large non-linear PTC is associated with the Curie temperature of the ceramic material and can be adjusted by adjusting the composition and manufacture of the ceramic material.

Heater 18 as used in various tests described herein was substantially flat, about like a 2 mm thick postage stamp or coin, with electrodes 20, 22 on its broad faces oriented approximately parallel to the fuel surface. The volume of test cell 10, 10', 80, 90 can also be small, typically about 10–25 cubic centimeters. Thus, it is not necessary to consume a large quantity of fuel in order to obtain the fuel DI according to the present invention.

Figure 2:
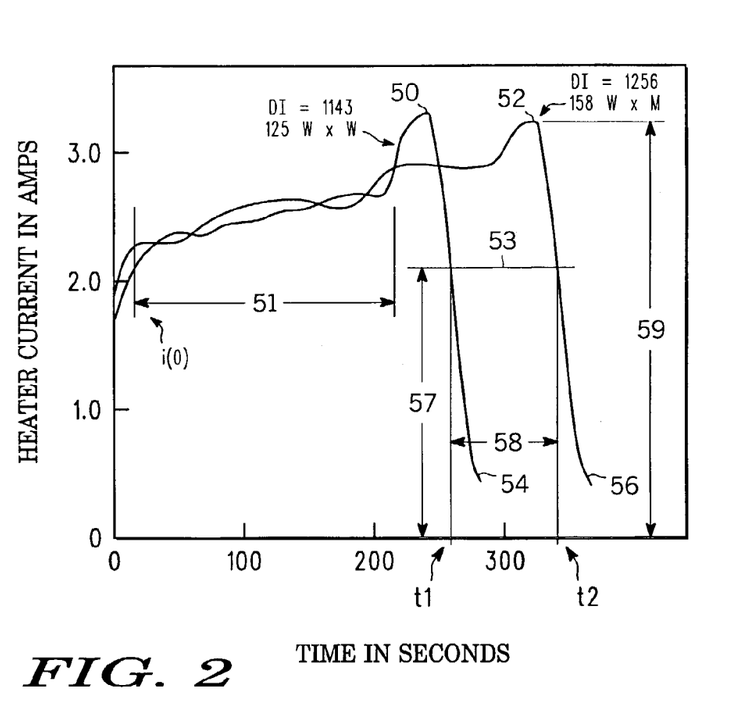
FIG. 2 is graph of test cell heater current versus time according to the present invention.

It has been found that when fuels having different DI values are heated as described above, and the current draw of heater 18 under constant voltage is plotted as a function of time, that markedly different characteristic curves are obtained for fuels with various known DI values. This is illustrated in FIG. 2 where the heater current is plotted against time for two fuels having RVP of about 7 and DI values of about 1143 and 1256 respectively. It will be noted that the current drawn by heater 18 changes only slowly with time in NTC region 51 during which the bulk of fuel portion 16U is vaporizing. As the level of fuel 16 begins to approach the position of heater 18 the current rises rapidly to peaks 50, 52' and then plunges sharply in regions 54, 56 where heater 18 has fully entered its large non-linear PTC regime. The heater current falls rapidly because the heater resistance is rising rapidly. This corresponds to the level of fuel 16 in cell 10 about reaching level 30D where heater 18 is now substantially no longer immersed in fuel 16 and its temperature can rise rapidly to $T_C$.

At or near $T_C$ the resistance of heater 18 rises so rapidly that current flow is substantially decreased, and effectively stops as shown by rapid current fall-off regions 54, 56. The times $t_1$, $t_2$ and the energy E required to reach rapid fall-off regions 54, 56, differ by amount 58 depending on the DI value of the fuel. The values of $t_1$, $t_2$ and the corresponding energy values are usefully determined when the heater current has fallen to level 53. Level 53 corresponds to the ratio R determined by the ratio of current 57 at level 53 to current 59 at peak 50, 52. R is preferably in the range of about 20–80%, more preferably in the range of about 30–70% and even more preferably in the range of about 40–60%. Since the heater current falls rapidly (e.g., about –0.41 A/sec in these tests) and over a large range of current in regions 54, 56, the exact choice or R is not critical and can be chosen as a matter of convenient measurement circuitry.

Alternatively, the rate of change of current (di/dt) can be used to determine when heater 18 has reached rapid fall-off region 54, 56. Those of skill in the art will understand that the magnitude of di/dt will depend upon the design of heater 18 for the particular application being used. However, if the average values of di/dt encountered in region 51 prior to peaks 50, 52 is compared to the average value of di/dt in rapid fall-off region 54, 56, there is a large change in magnitude and often a change in sign as well. For the data shown in FIG. 2, the average value of di/dt in region 51 [i.e., $(di/dt)_{51}$] is about +0.0024 A/sec and the average value of di/dt in regions 54, 56 [i.e., $(di/dt)_{54,56}$] is about –0.41 A/sec. Thus, the slope ratio SR $=|(di/dt)_{54,56}|/|(di/dt)_{51}|$ is about 170 for the data of FIG. 2. While such large SR values are preferred, an SR value of about 10 or larger is useful for determining when time measurement $t_1$, or $t_2$ should be made.

The area under the current versus time (i,t) curve at constant voltage (e.g., about 10.5 volts) gives the energy E consumed (i.e., E=i×v×t where i is the measured current, v is the constant voltage and t is time). Thus, by measuring the heating time at constant voltage or equivalently the energy E consumed from start t=0, to t=$t_1$, one can use the observed $t_1$ or $t_2$ value, in connection with, for example, a look-up table stored in memory, to determine the DI value of the fuel being tested (the symbols $t_1$, $t_2$ and t1, t2 respectively are used interchangeably in the text and figures). The look-up table preferably contains data relating an observed value of $t_1$ to values of $t_1$ obtained on previously measured fuel samples of known DI. The DI value obtained from the look-up table can then be used by the engine control system to set the engine operating parameters, and can be particularly useful during the time period when steady-state feedback operation is not practical.

Figure 3:
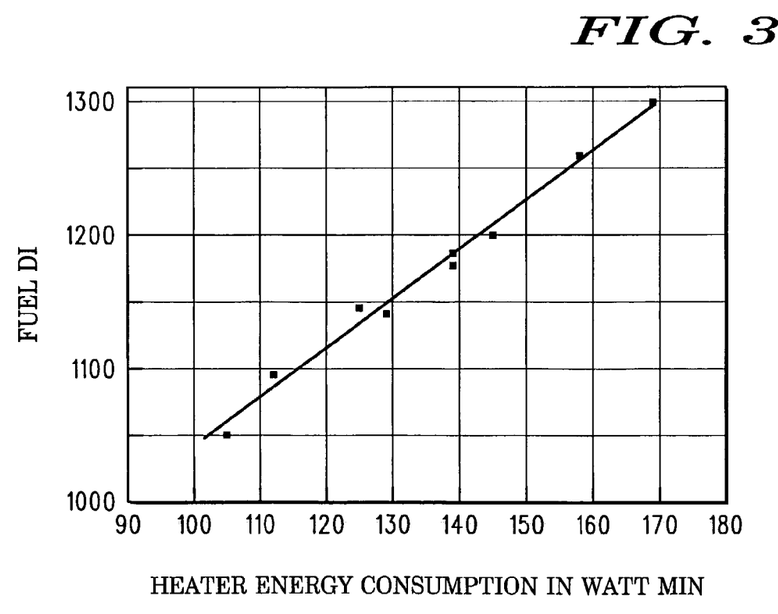
FIG. 3 is a graph of known fuel DI values versus test cell energy consumption obtained from measurements of the type shown in FIG. 2.

FIG. 3 is a plot of known fuel DI values versus heater energy consumption E (in watt-minutes) for various fuels to reach rapid fall-off portion 54, 56 of current versus time curves of the type illustrated in FIG. 2. The initial fuels temperatures $T_f$ were all about 82 degrees Fahrenheit at the beginning (t=0) of each test. It will be noted that there is a substantially linear relationship between the known fuel DI values and test cell heater energy consumption. Thus, the DI value of unknown samples can be computed using the following formula:

$$DI=k1*E(t1)+k2 \qquad [2]$$

where E is the energy consumed in watt-minutes (W×M) up to the time $t_1$ when heater current i is in the rapid fall-off region (e.g., region 54 in FIG. 2) and k1 and k2 are constants depending on the measurement conditions, e.g., fuel starting temperature $T_f$. For the data of FIG. 3 where $T_f$ was about 82 degrees Fahrenheit, k1 is about 3.9 and k2 is about 649. Different values are expected for $k1(T_f)$ and $k2(T_f)$ for different initial fuel temperatures $T_f$. Persons of skill in the art will understand how to obtain the values of $k1(T_f)$, $k2(T_f)$ for different starting fuel temperatures $T_f$ and how to evaluate such an equation.

While $T_f$ can be obtained by direct measurement using temperature sensor 13 (or sensor 61 in FIG. 4), this is not essential. It has been observed that the initial heater current i(0) at or shortly after heater 18 is switched on, correlates with $T_f$. Thus, by measuring i(0), and comparing this value with values obtained for known initial fuel temperatures stored in a correlation matrix in on-board memory, $T_f$ can be determined without the use of fuel temperature sensors 13 or 61 shown in FIGS. 1, 4, 5.

Figure 4:
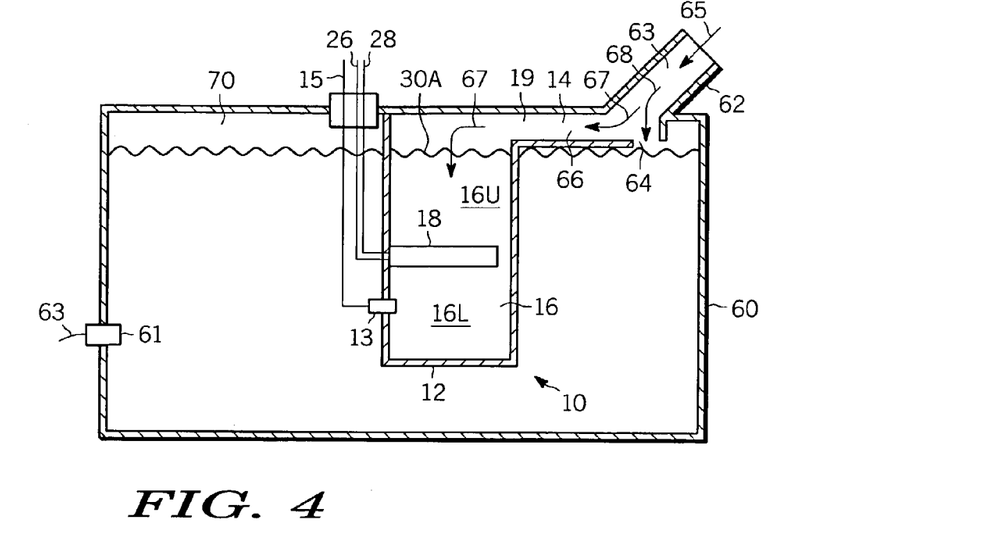
FIG. 4 is a simplified cross-sectional schematic view of a fuel test cell similar to FIG. 1, mounted inside a fuel tank.

FIG. 4 is a simplified schematic view of test cell 10 shown in FIG. 1, located inside vehicle fuel tank 60. Fuel tank 60 has fill-pipe 62 with inlet 63, outlet 64 leading into tank 60 and into test cell inlet 14. Outlet 64 and test cell inlet 14 are arranged to that portion 67 of fuel flow 65 goes into cell 10 and portion 68 of fuel flow 65 goes into tank 60. With this arrangement, any time that fuel is added to tank 60, test cell 10 is filled to level 30A and the properties of fuel 65 placed in tank 60 can be determined as explained above. Outlet 64 also vents test cell 10 to vapor space 70 at the top of tank 60 to provide for escape of vapors 19 coming from test cell 10. Fuel temperature sensor 61 with external lead 63 can be provided in tank 60 to measure the fuel temperature $T_f$ in the tank. Alternatively, temperature sensor 13 with external lead 15 can be provided on test cell 10, but these are not essential. The exact manner of determining the fuel temperature is not important so long as it provides reasonably accurate measurements or estimates of initial fuel temperature $T_f$.

Figure 5:
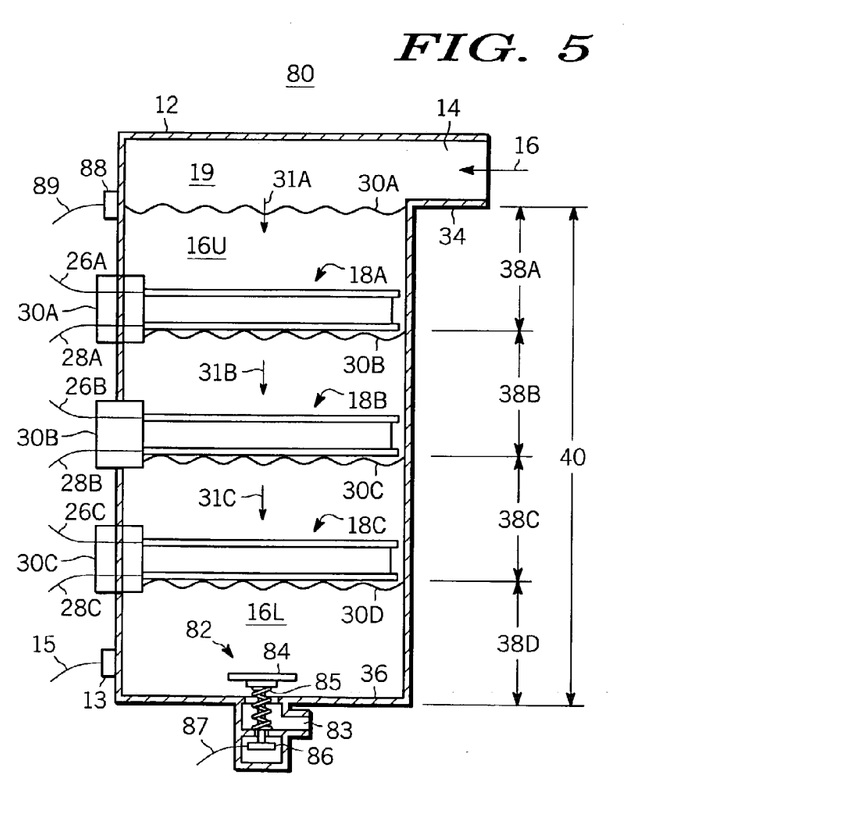
FIG. 5 shows a schematic cross-sectional illustration similar to FIG. 1 of a fuel test cell according to another exemplary of the present invention.

FIG. 5 shows a schematic cross-sectional illustration similar to FIG. 1 of test cell 80 according to a further exemplary embodiment of the present invention. Test cell 80 differs from test cell 10 of FIG. 1 in that multiple heaters 18A, 18B, 18C are included and drain 82 is provided at the bottom of cell 80. As those of skill in the art will understand, test cells may be equipped with multiple heaters or drains or both. They need not be combined.

Drain 82 permits cell 80 to be emptied of remaining fuel portion 16L after the DI measurement is completed. This is desirable so that when fresh fuel is placed in cell 80 it is not mixed with residual fuel 16L. For example, valve 84 actuated by solenoid 86 is opened to empty test cell 80 through drain 82 and outlet 83. Solenoid 86 is actuated via electrical lead 87. Tension spring 85 is conveniently provided to hold valve 84 closed when solenoid 86 is not energized. While drain 82 and valve 84 are shown located in bottom 36 of test cell 80, this is not essential and any manner of providing an openable drain for cell 80 can be used. In FIG. 5, valve 84 is shown in the open position actuated by solenoid 86 with spring 85 in tension.

Multiple measurement heaters 18A, 18B, 18C similar to heater 18 of FIG. 1 are provided in test cell 80 located in this example at about the 25%, 50% and 75% heights within cell 80, that is, with distances 38A, 38B, 38C and 38D all about 25% of distance 40, but this is not essential. As those of skill in the art will understand, multiple heaters may be placed at any useful location within the test cell, generally within a zone of about 20% to 80% of cell height 40, but this is not limiting. For example, an auxiliary heater may be placed on bottom 36 of test cell 10, 80 simply to reduce the fuel heating time.

While three measurement heaters are shown in FIG. 5, those of skill in the art will understand that any number of heaters may be used. As used herein the phrase "one or more heaters" is intended to encompass this and not be limiting. The measurement heaters 18A, 18B, 18C function in substantially the same way as described in connection with heater 18 of FIGS. 1, 4 and the heating results illustrated in FIGS. 2–3. Heaters 18A, 18B, 18C may be energized all at the same time at, for example, t=0 or maybe energized sequentially. Either arrangement is suitable. It is preferred to energize the multiple heaters at the same time since this reduces the test cycle time, i.e., fuel distillation occurs more quickly, but this is not essential.

Initially fuel 16 is at or near level 30A. As heaters 18A, 18B, 18C are energized (together or sequentially), the level of fuel 16 drops as shown by arrow 31A. When the fuel surface reaches level 30B so that upper heater 18A is uncovered from liquid fuel 16, heater 18A behaves in the same way as single heater 18 of FIGS. 1–3 and a time value $t_{A1}$ is obtained corresponding to rapid fall-off region 54 of heater 18A. Heater 18A effectively shuts off and may be de-energized. As heating continues using one or both of heaters 18B, 18C, the level of fuel 16 continues to drop as shown by arrow 31B and when level 30C is reached, heater 18B undergoes the rapid impedance change previously described and time value $t_{B1}$ corresponding to rapid fall-off region 54 for heater 18B is obtained. Similarly with heater 18C which provides time value $t_{C1}$ when fuel 16 reaches level 30D. Thus, by using multiple heaters, one obtains successive distillation times $t_{A1} < t_{B1} < t_{C1}$ representing the time required to distill away successive fractions of fuel 16.

Using multiple heaters has the advantage that by measuring the time differences, e.g., $(t_{C1}-t_{B1})$, $(t_{B1}-t_{A1})$ and/or $(t_{C1}-t_{A1})$, etc., depending on the number of heaters used, the effect of different initial fuel temperatures on the measured values is largely removed and information may also be obtained on the fuel composition, that is, for example, the presence or absence or proportions of fuel mix elements having different volatility values. Test cell 80 with multiple heaters is in effect a kind of fractional distillation column for separating fuel components of different volatility from the fuel mix. For example, if alcohol is present in the fuel in significant amounts, the time required to evaporate a given fraction of the fuel in the cell can increase dramatically. If this is observed, then alcohol is likely present and engine operating conditions can be adjusted accordingly.

Figure 6:
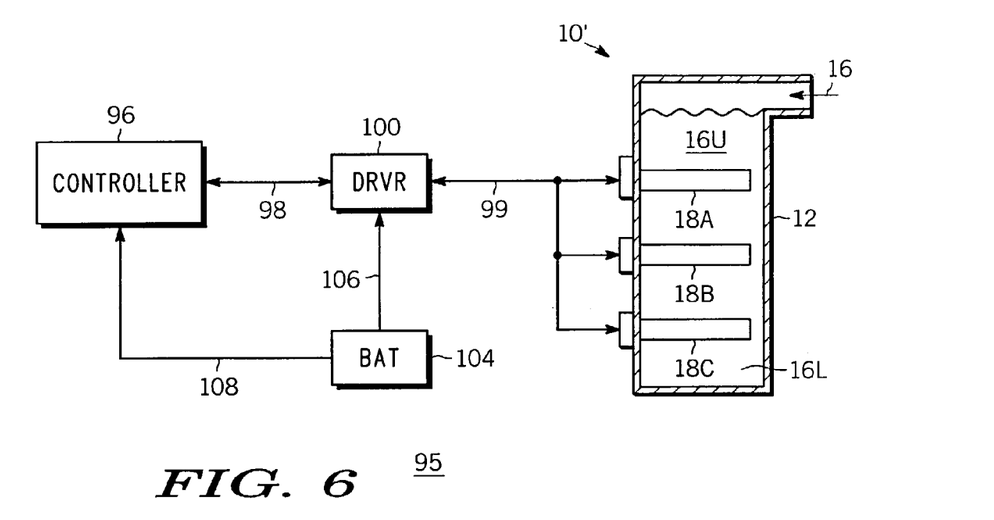
FIG. 6 is a simplified schematic diagram of an electrical system for operating a fuel test cell of the type illustrated in part in FIGS. 1, 4, 5 and 8.

FIG. 6 is a simplified schematic diagram of electrical system 95 for operating fuel test cell 10' similar to the types illustrated in FIGS. 1, 5. In FIG. 6 only heaters 18A–C are shown in cell 10'. Other elements such as level sensors, temperature sensors, drain values, etc., are omitted for simplicity. Controller 96 is coupled by bus 98, 99 through optional driver 100 to heaters 18A–C of cell 10'. Battery 104 supplies power to controller 96 and driver 100 via leads 108, 106. Leads 26A–C, 28A–C (see FIG. 5) from heaters 18A–C of test cell 10' are coupled to bus 99 so that, for example, each heater 18A–C can be energized, de-energized and measured independently. Optional driver 100 is desirable if the I/O circuitry of controller 96 (See FIG. 9) is not capable of supplying the power required by heaters 18A–C, depending upon the particular test cell design. If the power requirements of heaters 18A–C are within the drive capability of the I/O circuits of controller 96, then driver 100 maybe omitted. Persons of skill in the art will understand that system 95 functions with one or more heaters and that the three heaters shown are merely for convenience of explanation. Thus, if only heater 18B is included, test cell 10' is equivalent to single heater test cell 10 of FIG. 1.

Figure 7:
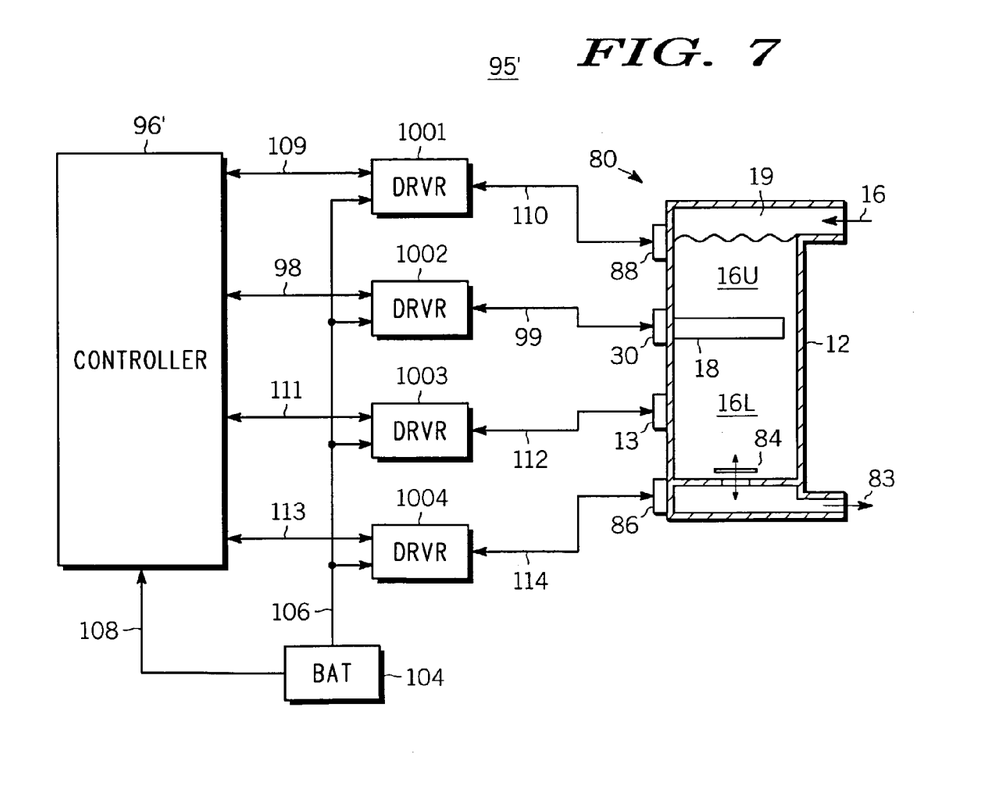
FIG. 7 is a simplified schematic diagram of an electrical system for operating a fuel test cell of the type illustrated in part in FIGS. 1, 4, 5 and 8.

FIG. 7 is a simplified schematic diagram of an electrical system 95' for operating fuel test cell 80 of the type illustrated in FIG. 5, but for simplicity only one heater 18 is illustrated. Persons of skill in the art will understand that one or more heaters can be used in connection with system 95'. Controller 96' is similar to controller 96 of FIG. 6 but has more operational I/O channels for interfacing with additional sensors and or operating parts of fuel test cell 80. Controller 96' is coupled to heater 18 through bus 98, 99 via optional driver 1002. Controller 96' is coupled to level sensor 88 through bus 109, 110 via optional driver 1001. Controller 96' is coupled to temperature sensor 13 through bus 111, 112 via optional driver 1003. Controller 96' is coupled to drain valve actuator 86 through bus 113, 114 via optional driver 1003. Battery 104 supplies power to controller 96' and drivers 1001–1004 via leads 108', 106'. As noted in connection with system 95 of FIG. 6, drivers 1001–1004 are optional depending upon the drive capabilities of the I/O channels of controller 96' and the power requirements of heater 18, level sensor 88, temperature sensor 13, and drain valve actuator 86.

Figure 8:
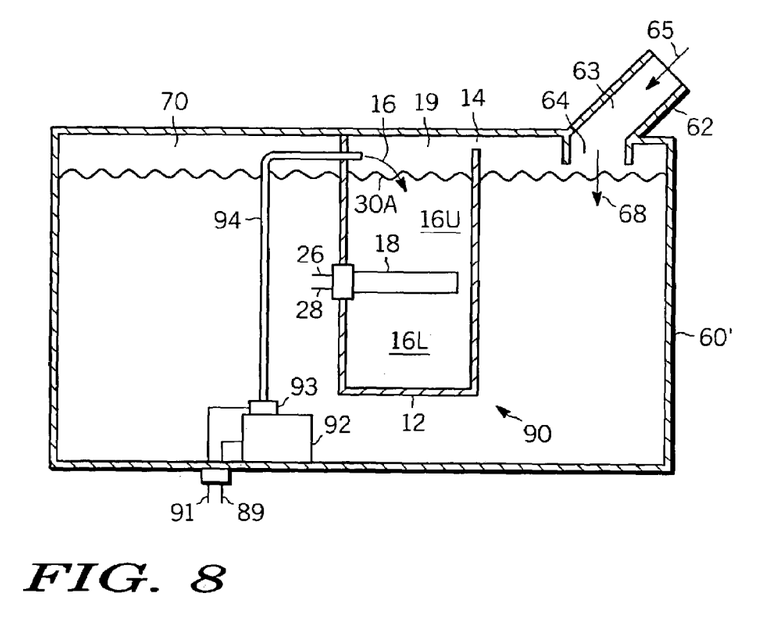
FIG. 8 is a simplified schematic cross-sectional view illustrating a fuel test cell mounted in a fuel tank, according to another exemplary embodiment of the present invention.

FIG. 8 is a simplified schematic cross-sectional view illustrating fuel test cell 90 mounted in fuel tank 60', according to a further exemplary embodiment of the present invention. Fuel test cell 90 differs from test cell 10 in that it is accompanied by fuel pump 92 and optional fuel valve 93 in tank 60'. Fuel pump 92 is coupled to test cell 90 via narrow conduit or tube 94 to supply fuel 16 to test cell 90. Otherwise, test cell 90 operates in the same manner as test cell 10 (or test cell 80). The connection from heater leads 26, 28 to the outside of tank 60' have been omitted for simplicity. Pump 92 is preferably the main vehicle fuel pump and tube 94 is a small bleed tube coupled to the normal output (not shown) of pump 92 supplying the engine. Thus, a separate pump is not required for the operation of test cell 90. Optional fuel valve 93 may be provided between pump 92 and test cell 90 to control the amount and/or the timing of delivery of fuel 16 to test cell 90. Leads 89, 91 couple pump 92 and valve 93 to a controller preferably outside of tank 60'. While pump 92 and valve 93 are shown as being located inside tank 60', this is merely for convenience of explanation and is not essential. One or both of pump 92 and valve 93 can be located outside of tank 60' but coupled thereto to receive fuel from tank 60'.

Figure 9:
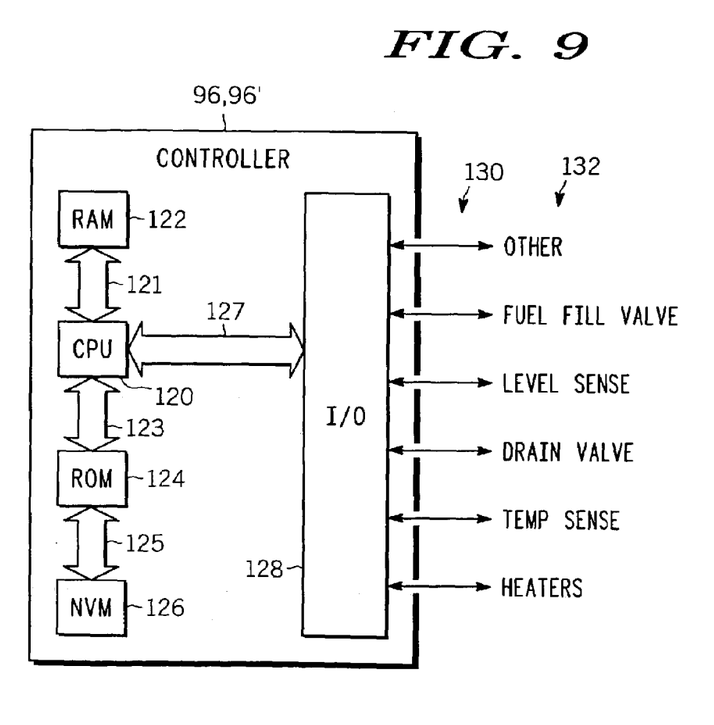
FIG. 9 is a simplified schematic diagram of a controller for operating the fuel test system of the present invention.

FIG. 9 is a simplified schematic diagram of controller 96, 96' for operating fuel test system 95, 95' of the present invention. Controller 96. 96' comprises central processor unit (CPU) 120 coupled to random access memory (RAM) 122, read only memory (ROM) 124, non-volatile memory (NVM) 126 and I/O 128 by buses 121, 123, 125, 127. Program code stored in ROM 124 (see for example, FIG. 10) is processed by CPU 120 in conjunction with memories 122, 124, 126 to send commands and receive inputs via I/O 128, storing non-volatile parameters to be remembered in NVM 126. Bus lines 130 couple I/O 128 to various sensors or actuators 132, for example, heater(s) 18, fuel temperature sensor 13, 61, drain valve actuator 86, level sensor 88, fuel valve 93 and/or fuel pump 92, and other elements not shown.

For example, in connection with test cells 10, 10', 80, 90 controller 96, 96' determines the initial fuel temperature $T_f$ by using temperature sensor 13, 61 or equivalent or otherwise estimating the initial fuel temperature, actuates heater 18, measures the instantaneous and/or integrated heater current as a function of time, detects the time or energy value E(t) when the heater current enters fall-off region 54, 56 and uses, for example, the measured E(t) value corresponding to $t_1$ for when the heater current reaches level 53 to calculate a DI value for the on-board fuel according to Eq. [2] in conjunction with predetermined values for $k1(T_f)$ and $k2(T_f)$ stored in memory 124 or 126. The measured DI value is then stored in NVM 126 for use by the engine controller in adjusting the operating parameters of the engine (not shown) to maximize performance and minimize pollution. Controller 96, 96' may be a stand-alone controller for operating test cells 10, 10', 80, 90 or the same controller that is also managing the engine or power train functions of the vehicle. Either approach is satisfactory although having one controller perform both functions is usually less costly.

Figure 10:
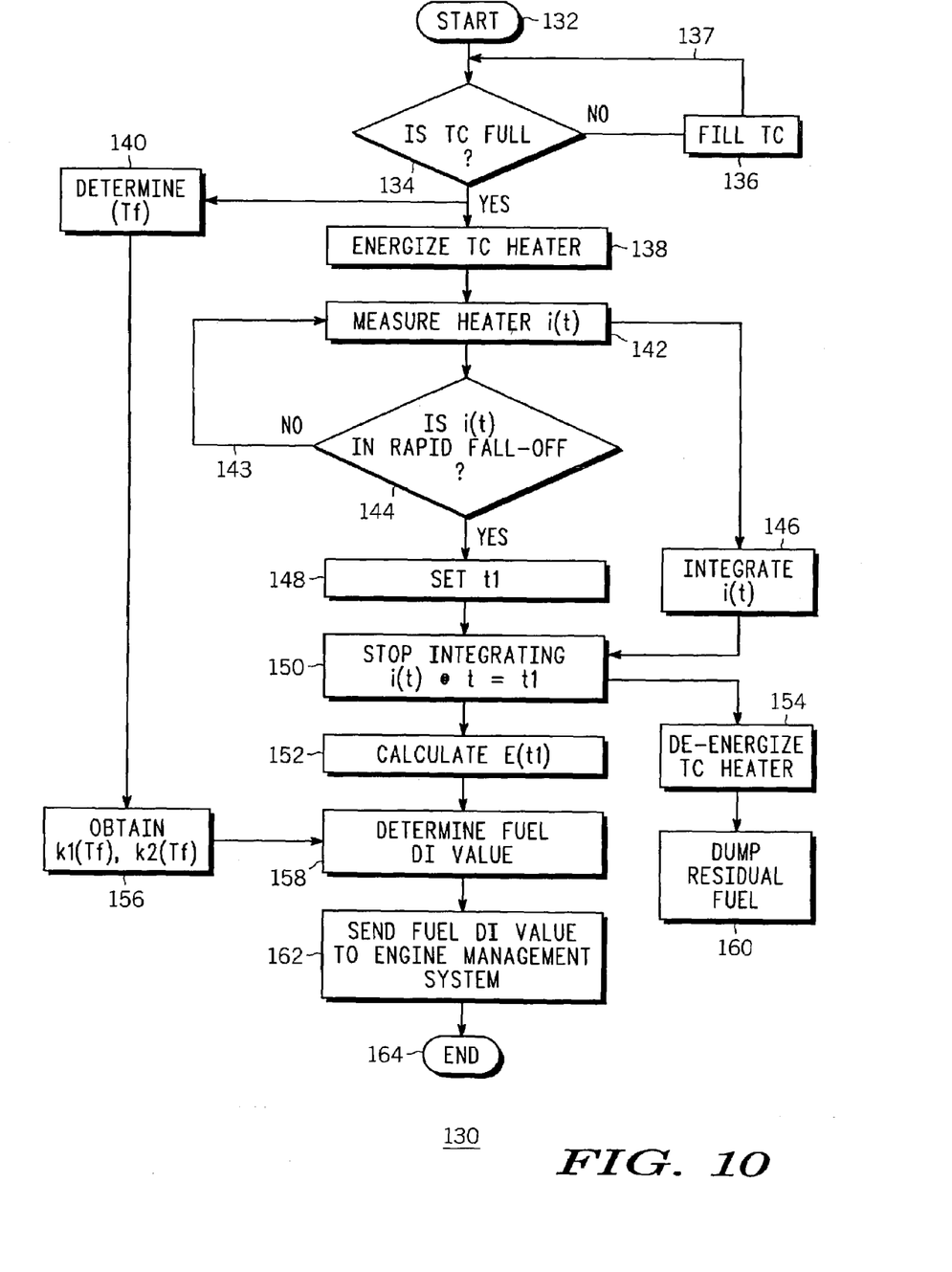
FIG. 10 is a flow chart according to the present invention illustrating a sequence of steps for determining a DI value of onboard fuel for use by an engine controller for adjusting the operating conditions of the engine.

FIG. 10 is a flow chart illustrating sequence 130 by which controller 96, 96' determines a DI value of onboard fuel 16 using test cell 10, 10', 80, 90 of the present invention and makes that DI value available to the engine controller for adjusting the operating conditions of the engine. The DI value so determined may be exported to a separate engine controller or used internally in controller 96, 96' if one controller is being used for both DI measurement and engine control functions. Flow chart 130 of FIG. 10 illustrates the method for a single heater system.

Following START 132, step 134 is a query that determines whether fuel test cell (abbreviated "TC") is full of fuel 16 or not. The TC can be any of those 10, 10', 80, 90 illustrated above. Query step 134 can be accomplished by interrogating level sensor 88 (see FIGS. 5, 7) or determining whether fuel tank 60 has been refilled since the last test thereby filling TC 10 as illustrated in FIG. 4, or whether fuel pump 92 illustrated in FIG. 8 has been running for a sufficient period to fill test cell 90 illustrated in FIG. 8, or in other ways that will occur to persons of skill based on the description contained herein.

If the response to query 134 is "NO," then in step 136 pump 92 and valve 93 can be activated to fill test cell 90 as in FIGS. 7–8 and the sequence returns to query step 134 as shown by return loop 137. Alternatively, the remaining steps can be delayed until tank 60 is refilled if the implementation being used corresponds to FIG. 4. If the response to query 134 is "YES," then in step 138 TC heater 18 is energized to begin the measurement for determining the DI value of the on-board fuel. In step 140, which can be performed at any time after step 134 and before step 156, fuel temperature $T_f$ is determined by direct measurement using temperature sensors 13 or 61 (see FIGS. 1, 4, 5, 7) or by estimation as previously explained or by other means known to those of skill in the art.

After heater 18 is energized in step 138, heater current i(t) is measured in step 142 and integrated as a function of time t in step 146. Step 144 is a query step in which it is determined whether the current versus time response i(t) of heater 18 has reached a rapid fall-off region (e.g., see 54, 56 in FIG. 2). As previously discussed in connection with FIG. 2, any convenient means may be used to determine whether i(t) is in rapid fall-off region 54, 56, e.g., at level 53 in FIG. 2. If the answer to query step 144 is "NO" then measurement step 142 continues, as shown by return loop 143. If the response to query step 144 is "YES" then in step 148 the present value of t, for example t1 in FIG. 2, is noted or SET and used in step 150 to stop integration of i(t) at t=t1. The integrated value of i(t) from t=0 to t=t1 is desirably used in step 152 to calculate the corresponding energy value of E(t1) by multiplying the integrated current value by the substantially constant voltage v applied to heater 18 during the integration period. Alternatively, if the voltage v is not constant, the incremental product v(t)×i(t) can be determined for each value of t and the product integrated from t=0 to t=t1 to give E(t1). Either method suffices.

In step 156, the previously determined fuel temperature $T_f$ is used to obtain the corresponding values of $k1(T_f)$ and $k2(T_f)$ which have been, for example, previously determined by analysis of a family of graphs of the type shown in FIG. 3 for known DI value fuels tested using different values of $T_f$ and the resulting values of $k1(T_f)$ and $k2(T_f)$ stored in controller 96, 96'. With this arrangement a knowledge of $T_f$ allows the corresponding $k1(T_f)$ and $k2(T_f)$ values to be retrieved from memory 124 or 126. In step 158, these values of $E(t_1)$ and $k1(T_f)$ and $k2(T_f)$ are used to determine a DI value for the on-board fuel. This can be accomplished, for example, by means of equation [2]. Alternatively, the $T_f$, E parameter values can be used in connection with a look-up table stored in memory 124 or 126 or elsewhere to give values for DI. Those of skill in the art will understand based on reading the present description that other means of converting $T_f$, E values to DI values can also be used.

In step 154, TC heater 18 is de-energized and in optional step 160 valve 84 (see FIGS. 5, 7) or equivalent is used to dump residual fuel 16L back into the general fuel tank or elsewhere. Other means for removing residual fuel 16L can also be used if that is desired. It is preferred that residual fuel 16L be removed so as to not adversely influence future DI measurements. In step 162, the DI value determined in step 158 is sent to the engine management or engine control system for use in optimizing engine operation and reducing exhaust pollution. The measurement sequence ends at 164. Sequence 130 can be performed when the engine is running or stopped. Thus, the on-board fuel DI value can be determined whenever the fuel system is opened to add more fuel and this value used until further fuel is added to the tank. Thus, the present invention makes it possible for the engine to always have available the DI value of the current fuel mix in the tank. This is extremely useful in improving engine operation and reducing pollution, especially during the initial cold-start period.

While FIG. 10 illustrates flow chart 130 for a single heater arrangement, those of skill in the art will understand based on the description herein how to determine t1 and E(t1) values for multiple heaters. For example, steps 138–158 are repeated for each successive heater 18A, 18B, 18C, etc. to produce successive values of $t1=t_{A1}$, $t_{B1}$, $t_{C1}$, etc., and $E(t1)=E(t_{A1})$, $E(t_{B1})$, $E(t_{C1})$, etc. Appropriate k1, k2 values can be obtained from memory for step 158 to determine relevant DI values or other fuel volatility parameters. By temporarily storing successive values of $t_{A1}$, $t_{B1}$, $t_{C1}$, etc., and/or $E(t_{A1})$, $E(t_{B1})$, $E(t_{C1})$, etc., one-or more subtraction steps can be used to obtain differences in $t_{A1}$, $t_{B1}$, $t_{C1}$, etc., and/or differences in $E(t_{A1})$, $E(t_{B1})$, $E(t_{C1})$, etc., for use in evaluating fuel composition and other properties and temperature normalization, as explained earlier, which are then sent to the engine management system in step 162. Further, by measuring successive values of $t_{A1}$, $t_{B1}$, $t_{C1}$, etc., and/or $E(t_{A1})$, $E(t_{B1})$, $E(t_{C1})$, etc., and differences therein, it is no longer necessary to measure $T_f$ in step 140 since the multiple heaters provide a repeatable environment for determining distillation times $t_{B1}$, $t_{C1}$, etc., and/or energy values $E(t_{B1})$, $E(t_{C1})$, etc., and constants k1, k2. Those of skill in the art will understand, therefore, that step 140 is not necessarily used after $t_{A1}$, etc.

While the preferred embodiments have been presented in the foregoing detailed description, it will be understood by those of skill in the art that many variations of the embodiments exist based on the information provided herein. For example, while different test cells 10, 10', 80, 90 have been illustrated with various combinations of elements in addition to heater(s) 18, persons of skill in the art will understand that other variations and combinations are possible and that coupling of these elements to system controller 96, 96' and the use of corresponding steps in the flow chart 130 can be changed accordingly. Further, while some of the illustrated embodiments are more convenient for use while the engine is stopped and others while the engine is running, either arrangement is useful. In addition, while the invented arrangement and method has been illustrated for use with gasoline fuels, it is also applicable to other fuels and fuel mixtures having various components with different distillation temperatures and vapor pressures.

Further, while the fuel properties have been characterized herein in terms of the distillation Drivability Index, those of skill in the art will understand that other fuel volatility measures could also be used by correlating a different volatility index against integrated heater current and time to evaporate a predetermined portion of the fuel in the test cell. Thus, the present invention is not limited merely to engine control systems based on the DI value. As used herein the terms "fuel properties", "fuel parameters", "fuel volatility index" and the like are intended to include other fuel volatility and composition measures and not be limited merely to the DI. Further the term "class of fuels" is intended to refer to fuels having a wide range of possible DI values and compositions that may be used in particular vehicle types and not to a specific fuel blend. Non-limiting examples of different classes of fuels are provided in ASTM D-4814.

It should also be appreciated that the exemplary embodiments are only examples, and are not intended to limit the scope, applicability, or configuration of the invention in any way. Rather, the foregoing detailed description provides those of skill in the art with a convenient roadmap for implementing the exemplary embodiments of the invention. Various changes may be made in the function and arrangement described in connection with the exemplary embodiments without departing from the spirit and scope of the invention as set forth in the appended claims.

The invention claimed is:

1. An on-board engine fuel properties measurement system comprising:
   a test cell for receiving a portion of on-board fuel;
   a heater mounted within the test cell for heating the fuel in the test cell, wherein resistance of the heater rapidly increases as a function of time as the temperature of the heater approaches a critical temperature;
   a circuit for measuring electrical properties, including electrical current, of the heater and determining an elapsed time until such rapid heater resistance increase occurs; and
   a controller for receiving the measured electrical properties and the elapsed time, the controller being configured to integrate the electrical current of the heater over the elapsed time to calculate an energy consumption value of the heater using the integrated electrical current value, wherein the energy consumption value of the heater is used to determine a fuel volatility index for the on-board fuel.

2. The system of claim 1 further comprising a connection for transmitting the calculated fuel volatility index to an engine management system.

3. The system of claim 1 wherein the heater has a critical temperature threshold that is above a fractional distillation temperature of a class of fuels used by the engine.

4. The system of claim 3 wherein the critical temperature threshold is above about $T_{50}$ for the class of fuels used by the engine.

5. The system of claim 1 further comprising a memory for storing information relating volatility of known fuels to the one or more fuel parameters determined by the system.

6. The system of claim 1 further comprising means for determining fuel temperature prior to erergizing the heater.

7. The system of claim 1, further comprising multiple heaters positioned within the test cell so that when the critical temperature of more than one heater is reached, between about 20% to 80% of the fuel in the test cell has been evaporated.

* * * * *